United States Patent
Bravo et al.

(10) Patent No.: US 9,516,892 B2
(45) Date of Patent: Dec. 13, 2016

(54) USE IN RUMINANTS OF A FOOD ADDITIVE INCLUDING A SWEETENER

(71) Applicants: PANCOSMA SA, Le Grand-Saconnex (CH); UNIVERSITY OF LIVERPOOL, Liverpool (GB)

(72) Inventors: David Bravo, Yverdon-les-Bains (CH); Soraya P. Shirazi-Beechey, Wirral (GB)

(73) Assignees: PANCOSMA S.A., Le Grand-Saconnex (CH); UNIVERSITY OF LIVERPOOL, Liverpool (GB)

( * ) Notice: Subject to any disclaimer, the term of this patent is extended or adjusted under 35 U.S.C. 154(b) by 0 days.

(21) Appl. No.: 14/424,918

(22) PCT Filed: Aug. 29, 2013

(86) PCT No.: PCT/EP2013/067907
§ 371 (c)(1),
(2) Date: Feb. 27, 2015

(87) PCT Pub. No.: WO2014/033217
PCT Pub. Date: Mar. 6, 2014

(65) Prior Publication Data
US 2015/0223494 A1    Aug. 13, 2015

Related U.S. Application Data

(60) Provisional application No. 61/695,259, filed on Aug. 30, 2012.

(30) Foreign Application Priority Data

Jan. 15, 2013 (FR) ..................... 13 50349

(51) Int. Cl.
*A01N 43/80* (2006.01)
*A61K 31/425* (2006.01)
*A23K 1/16* (2006.01)
*A61K 31/428* (2006.01)

(52) U.S. Cl.
CPC ............. *A23K 1/1628* (2013.01); *A23K 20/10* (2016.05); *A23K 20/137* (2016.05); *A23K 20/163* (2016.05); *A23K 50/10* (2016.05); *A61K 31/428* (2013.01)

(58) Field of Classification Search
None
See application file for complete search history.

(56) References Cited

U.S. PATENT DOCUMENTS 6,217,915 B1 * 4/2001 Luchansky ............ A23K 1/004
426/2

FOREIGN PATENT DOCUMENTS

JP         62-51938 A       3/1987

OTHER PUBLICATIONS

Hof, Christina; Use of Sweeteners in Animal Nutrition; Lohman information No. 24 (200) pp. 27-31.*
Reuter et al., "Effect of an artificial sweetener and yeast product combination on immune function measurements, growth performance and carcass characteristics of beef heifers", Journal of Animal Science, vol. 85, No. supplement 1, 2007, pp. 370 and 371 (cited in ISR).
J. P. McMenimen et al., "Effects of an artificial sweetener on health, performance, and dietarypreference of feedlot cattle", Journal of Animal Science, vol. 84, 2006, pp. 2491-2500 (cited in ISR).
C. Soulet, "Gut development is essential for weaning piglets", Internet, http://www.efeedlink.com/cps/attachment/2012/july/2012070513231678683448.pdf, Jul. 5, 2012, pp. 1 and 2 (cited in ISR).
R.J. Brown et al., "Non-Nutritive Sweeteners and their Role in the Gastrointestinal Tract", Journal of Clinical Endocrinology and Metabolism, vol. 97, No. 8, Jul. 7, 2012, pp. 2597-2606 (cited in ISR).
International Search Report dated Jan. 23, 2014, and Written Opinion of the International Searching Authority dated Jan. 23, 2014, issued in corresponding application No. PCT/EP2013/067907; in English (8 pages).

* cited by examiner

*Primary Examiner* — Jeffrey H Murray
(74) *Attorney, Agent, or Firm* — Westerman, Hattori, Daniels & Adrian, LLP

(57) ABSTRACT

The invention concerns the use of a food additive including a sweetener in the feed or the drink of a ruminant animal to reduce the impact of stressful conditions on intestinal mucosa quality.

21 Claims, 3 Drawing Sheets

USE IN RUMINANTS OF A FOOD ADDITIVE INCLUDING A SWEETENER

The invention relates to the use of a sweetener in food or drink of a ruminant animal, especially a calf.

Sweeteners are, as is known, used in animal food to give it a sweet taste and to make it more attractive. The sweet taste stimulates the appetite of the animal, which encourages him to eat more and thereby improves its weight gain. Sweeteners are especially used in the feeding of young animals such as calves, piglets and lambs in the growth phase. As an illustrative example of a sweetener used in animal feed, the product SUCRAM® from the company Pancosma can be quoted.

When an animal is subject to stressful conditions (for example heat stress, dramatic feed composition changes, oxidative stress . . . ), the animal reduces or stops momentarily his feed intake. However, deprivation of food in an animal, especially in young animals during growth, infringes dramatically and quickly the quality of the intestinal mucosa, especially growth, permeability, absorptive and immune functions of the mucosa. This degradation of the intestinal mucosa can consequently reduce animal resistance to enteropathogens and/or impairs animal overall production performance.

It is therefore necessary to find a simple and effective solution to reduce the damage to the intestinal mucosa due to stressful conditions in a ruminant animal.

To this end, the invention concerns the use of an additive comprising a sweetener in a ruminant animal food or drink to reduce the negative impacts of stressful conditions on animal intestinal mucosa quality, especially on growth, permeability, absorptive and immune functions of the mucosa, in order to maintain normal growth rate or production performance and/or improve animal resistance to enteropathogens.

The use of the additive can be performed through a preventive way or a curative way.

The term sweetener is meant as any substance or compound, chemical or natural, having a sweet taste. By "intense sweetener" is meant a sweetener with a sweetening power at least 20 times higher than sugar.

The additive can be administered to unweaned animal, especially in a preventive way, at a dose lower or equal to 400 grams of sweetener per ton of milk replacer under dehydrated form.

In a first embodiment, the additive is administered to the weaned animal, especially in a curative way:
  at a dose lower or equal to 200 grams sweetener per ton of feed in form of dry matter and/or
  at a dose lower or equal to 100 grams of sweetener per ton of drinking water.

In a second embodiment, the additive is administered to the weaned animal, especially in a curative way, at a dose lower or equal to 75 grams of sweetener/ton of drinking water and/or because a lower dose or equal to 150 grams of sweetener per ton of feed in form of dry matter.

In a third embodiment, the additive is administered to the weaned animal, especially in a curative way, at a dose lower or equal to 50 grams of sweetener/ton of drinking water and/or because a lower dose or equal to 100 grams of sweetener per ton of feed in form of dry matter.

The invention will be better understood from the following description of a particular embodiment of the use according to the invention with reference to the accompanying drawings in which.

Figure 1:
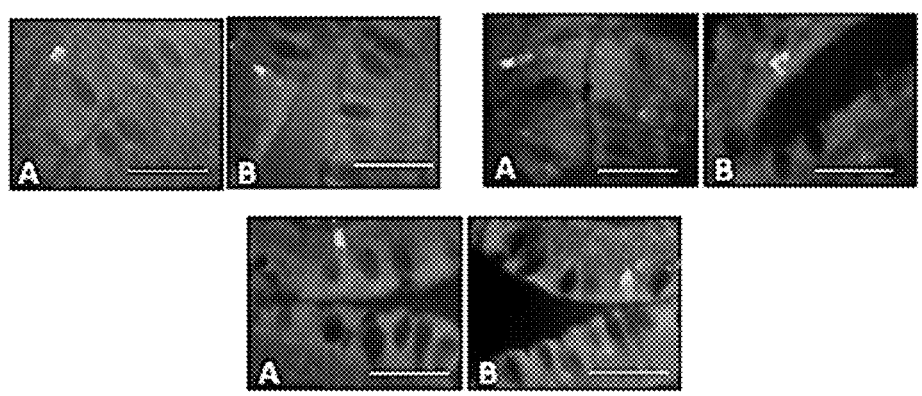
FIG. 1 shows images of un-weaned pre-ruminant calf intestinal cells.

The invention concerns the use of a food additive including a sweetener in the feed or the drink of a ruminant animal to reduce the impact of stressful conditions on intestinal mucosa quality. The additive is used especially to improve growth, permeability and/or absorption and immune functions of the intestinal mucosa, for example in case of heat stress, oxidative stress and/or major feed changes, especially at weaning. The food additive may be used on a preventive way and/or on a curative way. On a preventive way, the additive is used to improve intestinal mucosa quality, whereas, on a curative way, the additive is used to limit degradation of intestinal mucosa quality. In order to prevent a degradation of the mucosa quality, the additive is administrated before stressful conditions. During stressful conditions, the additive can also be administrated to reduce the impact of these stressful conditions on the intestinal mucosa. To this end, the invention also concerns the additive used as a medicament to limit degradation of intestinal mucosa, particularly caused in and after a stressful condition, or used for a prophylactic effect, particularly on the intestinal mucosa.

To observe the effects of a food additive corresponding to a sweetener in the intestine of a ruminant animal, the following experiment was performed.

The experiment was conducted in calves initially aged of one week. Four groups denoted G1, G2, G3 and G4, each comprising four calves are selected. The experiment consists of two phases:
  The first phase Ph_I, from the 1st day of the experiment, noted Day 1, to the 55th day of the experiment, noted Day 55
  A second phase Ph_II, from 56th day of experimentation (Day 56) and ending when the calves are older than 4 months.

The first phase Ph_I mimicks the use of the additive in a preventive way, whereas the second phase Ph_II mimicks the use of the additive in a curative way.

Groups G1 and G3 are control groups.

During the first phase Ph_I, calves of the four groups are fed a milk substitute or milk replacer. The milk replacer was given to calves from groups G1, G3 and G4 without sweetener. The milk replacer given to calves of group G2 product contains a sweetener. Calves of groups G1 and G2 are slaughtered after the first phase.

During the second phase Ph_II, calves groups G3 and G4 are fed a concentrate rich in starch. The concentrate given to calves group G3 is without sweetener. The concentrate given to calves G4 group contains the sweetener product.

Table 1 below summarizes the different treatments for the different groups.

TABLE 1

| Group | Phase (I or II) | Treatment |
|---|---|---|
| G1 | Ph_I | Milk replacer |
|    | Ph_II |  |
| G2 | Ph_I | Milk replacer with SUCRAM © |
|    | Ph_II |  |
| G3 | Ph_I | Milk replacer |
|    | Ph_II | Starch based concentrate |
| G4 | Ph_I | Milk replacer |
|    | Ph_II | Starch based concentrate with SUCRAM © |

The sweetener, or food additive, includes an intense sweetener. It may contain at least one of the compounds of the group consisting of saccharin, sodium saccharin, calcium saccharin, aspartame, acesulfame K, cyclamate and steviosides.

The sweetener (or additive) also contains a potentiator. The potentiator role is to extend the perception of sweetness and to hide the second taste or parasites of the sweetener (such as bitter or metallic tastes). It comprises at least one of the compounds from the group comprising glycyrrhizin, ammonium glycyrrhizinate, potassium glycyrrhizinate, sodium glycyrrhizinate, thaumatin, kokumi, neohesperidin dihydrochalcone, the ribotides and sodium glutamate.

The sweetener, or additive, comprises from 80% to 100% by weight of sweetener(s) and from 20% to 0% by weight of potentiator(s).

The sweetener (or food additive) used as an example of illustration in the experiment described here, is the product SUCRAM® C-150 of the Pancosma company. This product contains 80% by weight of sodium saccharin 10 and 20% by weight of potentiator(s).

For the experiment, the doses of sweetener product provided to Calves are the following:

Before withdrawal, the dose of 400 ppm Product SUCRAM® C-150 in the CMR (Calf Milk Replacer) or milk substitution, in dried form, i.e. before reconstitution, which corresponds to 40 ppm in milk substitute reconstituted (or rehydrated) (approximately 200 mg per animal per day or 0.4 to 5.7 mg per kg of live animal weight per day);

After weaning, the dose is either 200 ppm of SUCRAM® C-150 in the solid feed, or 100 ppm product SUCRAM® C-150 in the drinking water, which corresponds to a dose 200 to 2000 mg per animal per day (one dose of 1 to 35 mg per kg of live animal weight per day), the dose given be in solid food or in drinking water.

Figure 2:
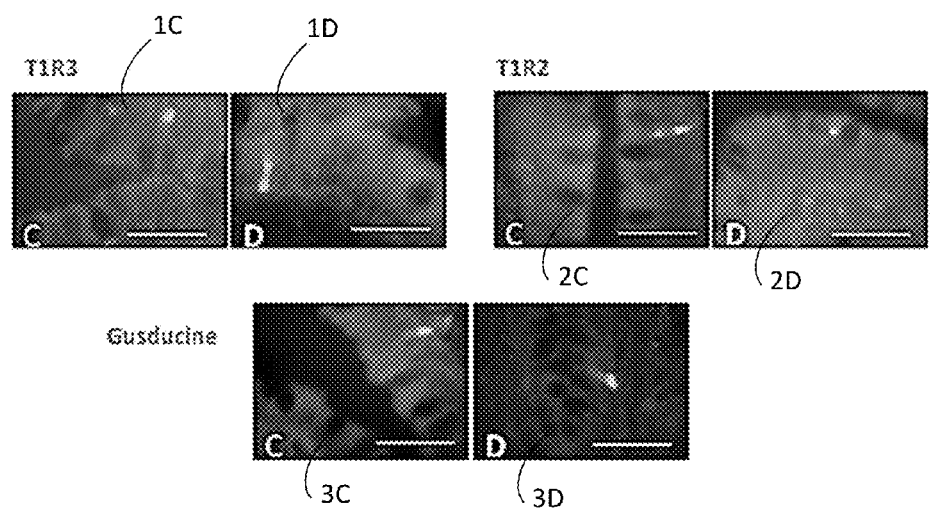
FIG. 2 shows images of weaned ruminant calf intestinal cells.
Figure 3:
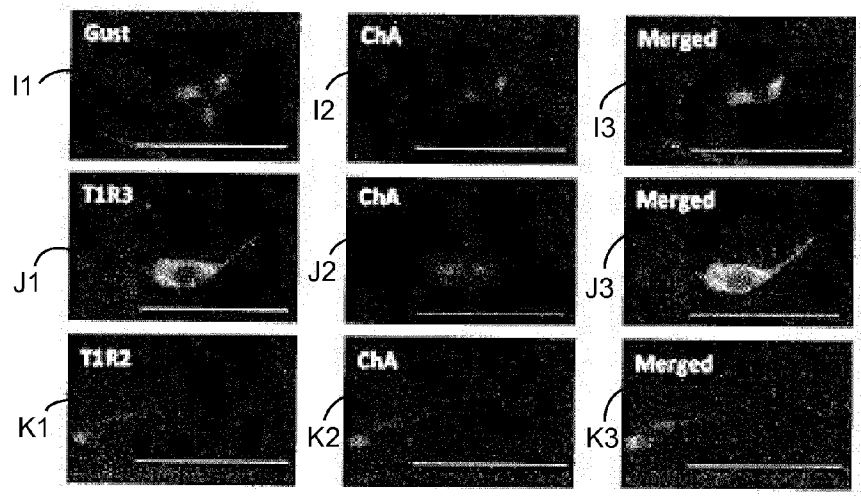
FIG. 3 shows images of weaned ruminant calf intestinal cells.

FIGS. 1, 2 and 3, discussed below, include images of calf intestinal cells. These images are enlarged by a factor 400 and the scale bar shown at the bottom of each image corresponds to a length of 10 microns.

FIG. 1 shows images of intestinal cells from un-weaned calf intestinal cells from G1 and G2 groups. Images marked "A" correspond to the calves of group G1 and images marked "B" correspond to the calves of group G2. Images 1A and 1B show the presence of the T1R3 protein in intestinal cells of calves from Groups G1 and G2. Images 2A and 2B show the presence of the protein T1R2 in intestinal cells calves from groups G1 and G2. The Images 3A and 3B show the presence of the protein gustducin, noted G, in calf intestinal cells from groups G1 and G2. These images show that the intestinal cells of pre-ruminant calves (that is to say, un-weaned) given a diet with or without sweetener, express receptors T1R2 and T1R3 taste and protein gustducin at mRNA level.

FIG. 2 shows images of intestinal cells of weaned calves from groups G3 and G4. Images marked "C" correspond to the calves of G3 and images marked "D" correspond to the calves of group G4. Images 1C and 1D show the presence of the T1R3 protein in intestinal cells of calves from groups G3 and G4. Images 2C and 2D show the presence of the protein T1R2 in intestinal cells calves groups from G3 and G4. The 3C and 3D pictures show the presence of the protein gustducin, noted G, in intestinal cells of weaned calves. The images show that the intestinal cells from ruminant calves (that is to say weaned), given a diet with or without sweetener express taste receptor T1R2 and T1R3, and protein gustducin, at mRNA level.

FIG. 3 contains images of enteroendocrine cells of ruminant calves from groups G3 and G4. In this FIG. 3, each line includes three images I1-I3, J1-J3 and K1-K3, from the same enteroendocrine cell. For each line, the third image (I3, J3 or K3) is a superposition of the first two pictures of this line (I1-I2, J1-J2, K1-K2). The first two images I1, I2 from the first line represent, respectively, in the same enteroendocrine cell, a gustducin protein and chromagranin A protein (ChA). The first two images of the second line, noted J1, J2, respectively represent, in the same enteroendocrine cell, a T1R3 receptor and chromagranin A protein (ChA). The first two images K1, K2 of the third line represent, respectively, in the same entero-endocrine cell, a T1R2 receptor and chromagranin A protein (ChA). The I3, J3 and K3 pictures show clearly, by superposition, that the T1R2 receptor, the T1R3 receptor and gustducin protein are co-located with a chromagranin A protein (ChA), which is a typical marker of enteroendocrine cells. This confirms the presence of T1R2 receptor T1R3 and Gustducin protein in enteroendocrine cells of weaned calves receiving a power supply with or without sweetener.

Results similar to those observed for calves ruminants the images in FIG. 3 were observed for pre-ruminant calves Groups G1 and G2.

The images of FIGS. 1-3 clearly show the presence in the intestine, post-rumen, of calves enteroendocrine cells comprising receptor T1R3 and T1R2 and gustducin. However, such enteroendocrine cells have a key role of specialized transducers of lumen intestinal content, as shown in FIG. 4.

However, the enteroendocrine cells, receptors T1R2 and T1R3 and Gustducin protein, present in the lower intestine or post rumen from pre-ruminant or ruminant calf, constitute the elements which are needed to implement cellular mechanisms triggered by a sweetener product leading to the maintenance of intestinal mucosa quality, as previously described for the pig.

Figure 4:
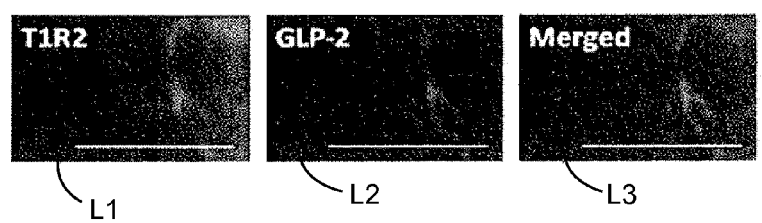
FIG. 4 shows images of a calf intestinal cell expressing GLP-2.

In FIG. 4 shows three pictures L1, L2, L3 of a calf enteroendocrine cell (ruminant or weaned) having ingested the sweetener product SUCRAM®. It is therefore a calf from group G2 or group G4. The first two images L1, L2 represent a T1R2 receptor and GLP-2 hormone, collocated in the same enteroendocrine cell.

The image L3 corresponds to a superposition of L1 and L2 images. In other words, the enteroendocrine cell shown on images L1-L3 is co-expressing the receptor T1R2 and GLP-2 hormone. This clearly shows that enteroendocrine cells of the calf are adapted to release the GLP-2 hormone.

Figure 5:
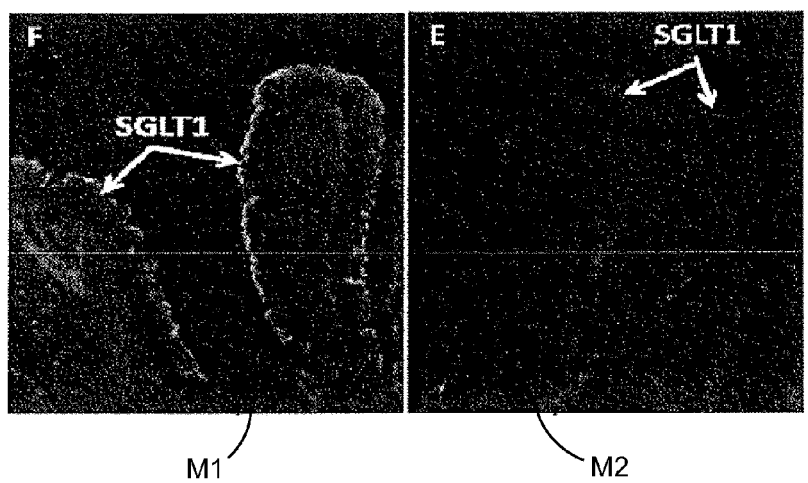
FIG. 5 shows images of intestinal BBMV (brush border membrane vesicles) from calves.

FIG. 5 shows two pictures M1 and M2 of vesicles isolated from the brush border membrane (BBMV—Brush Border-Membrane Vesicles). The images are enlarged by a factor of 200. The image M2 correspond to a ruminant calf or weaned not having ingested a sweetener product, i.e. a calf group G3. The image M1 refers to a ruminant calf or weaned which have ingested the sweetener SUCRAM® otherwise said a calf group G4. A visual comparison of the M1 and M2 pictures clearly shows the presence of the edges of the villi of the membrane "Brush-Border" a number of glucose transporters SGLT1 much higher for the calf that had ingested the sweetener SUCRAM® than for the calf that had not ingested any sweetener.

Figure 6:
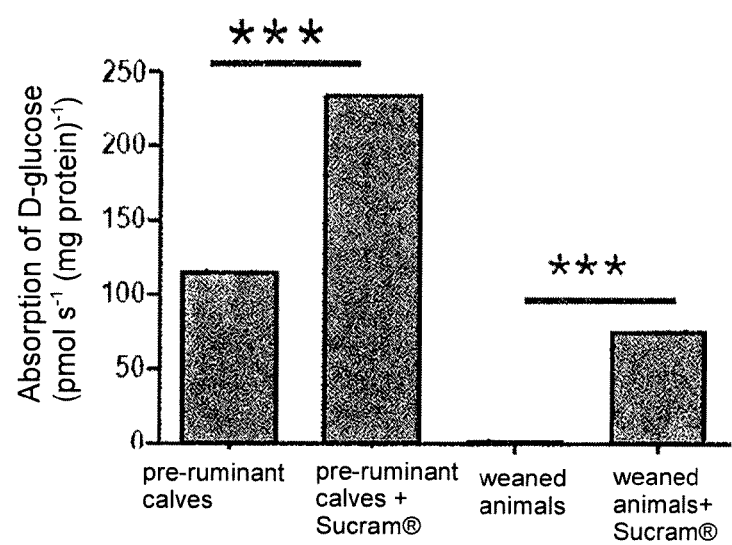
FIG. 6 shows a diagram of the consumption of D-glucose by calves of four test groups.

The graph in FIG. 6 shows the amount of D-glucose calves absorbed by the four groups G1-G4 in the form of a histogram. Columns g1, g2, g3 and g4 represent the amounts of D-glucose absorbed by the intestinal mucosa (simulated by the membrane "Brush-Border") calves of groups G1, G2, G3 and G4 in picomoles (Pmol) per second per milligram (mg) of protein.

With reference to FIG. 6, it is assumed that the absorption by the "Brush-Border" mucosa simulates the potential absorption of glucose by the intestinal mucosa.

It is observed in FIG. 6 that:
The amount of D-glucose absorbed by the un-weaned calves from group G2 (with SUCRAM®) is much higher than for un-weaned calves from group G1 (without SUCRAM®). The amount of D-glucose absorbed by calves in G2 group is almost twice greater than that of the calves from group G1;
The amount of D-glucose absorbed by the weaned calves from group G4 (with SUCRAM®) is much higher than that absorbed by weaned calves from group G3 (without SUCRAM®), which is almost zero.

These results indicate that the ability of glucose uptake by intestinal mucosa of weaned calves is increased by the presence of SUCRAM® product in the food. Provided that glucose is available for absorption after hydrolysis by pancreatic amylase starch un-degraded in the rumen, then this ability will be put to contribution and absorption will increase.

Images M1 and M2 and graph in FIG. 6 show that ingestion of a sweetening product such as SUCRAM® by calves before or after weaning has the effect of increasing the production of carriers SGLT1 glucose level of the intestinal mucosa and therefore to increase the capacity of calves gut to absorb glucose. The invention thus relates to the use of a food additive including a sweetener in food or drink for a calf to improve its intestinal mucosa quality.

In the foregoing description, the sweetener SUCRAM® C-150 is added to food or drink of the calf a dose 400 ppm SUCRAM® C-150 in the drink for pre-ruminant calves and 200 ppm in feed for ruminant calves.

The same effects on intestinal mucosa quality are obtained with the following uses:
a) usage in which the additive is administered to an un-weaned pre-ruminant animal in an amount lower or equal to 400 sweetener grams per ton of milk substitute in the dried form (corresponding to a dose lower or equal to 40 g sweetener per ton of reconstituted milk replacer);
b) usage in which the additive is administered to a weaned ruminant animal in an amount lower or equal to 200 grams of sweetener per ton of feed material in the form of dry or in an amount lower or equal to 100 grams sweetener/ton of drinking water (which corresponds to a dose from 200 to 2000 mg per animal per day or a dose from 1 to 34 mg per kg of animal live weight per day);
c) usage in which the additive is administered to the weaned animal in an amount lower or equal to 150 grams Sweetener per ton of feed as a dry material, and/or at a dose less than or equal to 75 grams of sweetener per ton of drinking water (which corresponds to a dose from 150 to 1500 mg per animal per day, and/or a dose from 1 to 25 mg per kg body weight animal per day);
d) usage in which the additive is administered to the weaned animal in an amount lower or equal to 100 grams sweetener per ton of feed as a dry material, and/or a dose lower or equal to 50 grams of sweetener per ton of drinking water (which corresponds to a dose from 100 to 1000 mg per pet, per day, a dose from 1-17 mg per kg body weight animal per day).

In addition, it was observed that the use of the additive a) to d) induced another effect such as the improvement of the growth of the animal. The invention disclosed also a use of an additive comprising a sweetener in food or drink of a ruminant animal to improve growth of the animal.

When the sweetener dose is lower or equal to 150 g per ton of food as dry matter (75 grams sweetener per ton of drinking water), it is not sufficient to give the food or drink a sweet taste. In this case, it does not make the food (or drink) more attractive in terms of taste for calves. However, this dose remains effective to trigger a physiological response inducing an improvement of intestinal mucosa quality. Thus the sweetener can be used at low dosages in food, not to give food a more attractive flavor, but to improve the architecture of the low intestine. This is beneficial at the intestinal level and induces some beneficial effects on animal overall performance, group homogeneity and resistance to diseases because of the major role of the intestine mucosa in the immune response.

It should be emphasized that the calf is a ruminant polygastric animal. His digestive system includes
an upper part comprising a plurality of pockets as the rumen, reticulum, omasum and abomasum, and
a lower part including the small intestine and the large intestine.

The rumen is the largest pocket. It acts as a fermenter. Food ingested by the calf undergo fermentation in the rumen. The majority of carbohydrates, also known as carbone hydrates, coming from ingested foods are fermented. This ruminal fermentation produces volatile fatty acids, which are absorbed by the blood at the level of the rumen wall essentially. These volatile fatty acids are the main energy source of the ruminant.

The ruminant gastric system differs considerably from the one of a monogastric animal which draws its energy mainly from carbohydrates and lipids absorbed from the intestine. We particularly emphasize that the vast majority, if not all, carbohydrates are fermented in the rumen. Very few carbohydrates are likely to be absorbed in the intestine. This result in a detection system to ensure the residual absorption of carbohydrates in the intestine in ruminants that appears to be neither useful nor cost-effective in terms of energy.

However, unexpectedly, it was found that the use of a sweetener product such as SUCRAM® in food or drink of a ruminant produces a reinforcing effect on intestinal mucosa quality.

The present invention is applicable to ruminants other than cattle.

The invention claimed is:
1. Method of reducing an impact of stressful conditions on intestinal mucosa quality of a ruminant animal, comprising:
administering a food additive in a feed or a drink of the ruminant animal so as to reduce the impact of the stressful conditions on the intestinal mucosa quality, wherein the food additive comprises a sweetener and a potentiator.

2. Method according to claim 1, wherein the food additive improves at least one of growth, permeability, absorption, and immune functions of the intestinal mucosa.

3. Method according to claim 1, wherein the food additive is administered in case of at least one of heat stress, oxidative stress, and major feed changes, especially at weaning.

4. Method according to claim 1, wherein the food additive is administered in at least one of a preventive way and in a curative way.

5. Method according to claim 4, wherein, in a preventive way, the food additive improves intestinal mucosa quality.

6. Method according to claim 4, wherein, in a curative way, the food additive limits degradation of intestinal mucosa quality.

7. Method according to claim 1, wherein the food additive is administrated before the stressful conditions.

8. Method according to claim 1, wherein the food additive is administrated during the stressful conditions.

9. Method according to claim 1, wherein the food additive is administered to an un-weaned animal at a dose lower or equal to 400 grams of sweetener per ton of dehydrated milk replacer.

10. Method according to claim 1, wherein the food additive is administered to a weaned animal at a dose lower or equal to 200 grams of sweetener per ton of feed as dry matter.

11. Method according to claim 1, wherein the food additive is administered to a weaned animal at a dose lower or equal to 100 grams of sweetener per ton of drinking water.

12. Method according to claim 1, wherein the food additive is administered to a weaned animal at a dose lower or equal to 150 grams of sweetener per ton of feed as dry matter.

13. Method according to claim 1, wherein the food additive is administered to a weaned animal at a dose lower or equal to 75 grams of sweetener per ton of drinking water.

14. Method according to claim 1, wherein the food additive is administered to a weaned animal at a dose lower or equal to 100 grams of sweetener per ton of feed as dry matter.

15. Method according to claim 1, wherein the food additive is administered to a weaned animal at a dose lower or equal to 50 grams of sweetener per ton of drinking water.

16. Method according to claim 1, wherein the sweetener is an intense sweetener.

17. Method according to claim 16, wherein the sweetener comprises saccharin.

18. Method according to claim 16, wherein the sweetener comprises at least one compound selected from the group consisting of sodium saccharin, calcium saccharin, aspartame, acesulfame K, stevioside and cyclamate.

19. Method according to claim 1, wherein the potentiator is at least one compound selected from the group consisting of glycyrrhizin, ammonium glycyrrhizinate, potassium glycyrrhizinate, sodium glycyrrhizinate, thaumatin, kokumi, neohesperidin dihydrochalcone, ribotides and sodium glutamate.

20. Method according to claim 1, wherein the food additive comprises from 0% to 20% by weight of potentiator(s).

21. Method according to claim 1, wherein the animal is a calf.

* * * * *